United States Patent [19]

Gnieser et al.

[11] 4,123,341
[45] Oct. 31, 1978

[54] APPARATUS AND PROCESS FOR TREATING CONTAMINATED WATER

[75] Inventors: Jurgen Gnieser, Weinfelden; Luciano Pelloni, Zurich, both of Switzerland

[73] Assignee: Sulzer Brothers Limited, Winterthur, Switzerland

[21] Appl. No.: 830,809

[22] Filed: Sep. 6, 1977

[30] Foreign Application Priority Data

Sep. 27, 1976 [CH] Switzerland .................. 12183/76

[51] Int. Cl.² .............................................. C02B 1/82
[52] U.S. Cl. .................................... 204/152; 204/149; 204/180 R; 204/228
[58] Field of Search ............ 204/149, 151, 152, 180 R, 204/299 R, 186, 302, 275, 228; 210/13, 14, 62

[56] References Cited

U.S. PATENT DOCUMENTS

| 3,975,247 | 8/1976 | Stralser | 204/152 |
| 4,001,100 | 1/1977 | Havdock | 204/180 R |
| 4,045,326 | 8/1977 | King | 204/299 R |

Primary Examiner—Arthur C. Prescott
Attorney, Agent, or Firm—Kenyon & Kenyon, Reilly, Carr & Chapin

[57] ABSTRACT

The water treatment apparatus is provided with one or more turbidity meters in the inlet line to the electrocoagulator and the outlet line from the flotation stage. The voltage across the coagulator electrodes is controlled in response to a controller which receives signals from the respective turbidity meters. When the turbidity increases in either the inlet line or outlet line, the voltage is increased and when the turbidity decreases, the voltage decreases. In addition, upon an increase in voltage above a top limit, compressed air is charged into the coagulator while the rate of flow of recycled sludge is increased. Also, the pressure in the coagulator is maintained during operation of the air compressor.

3 Claims, 1 Drawing Figure

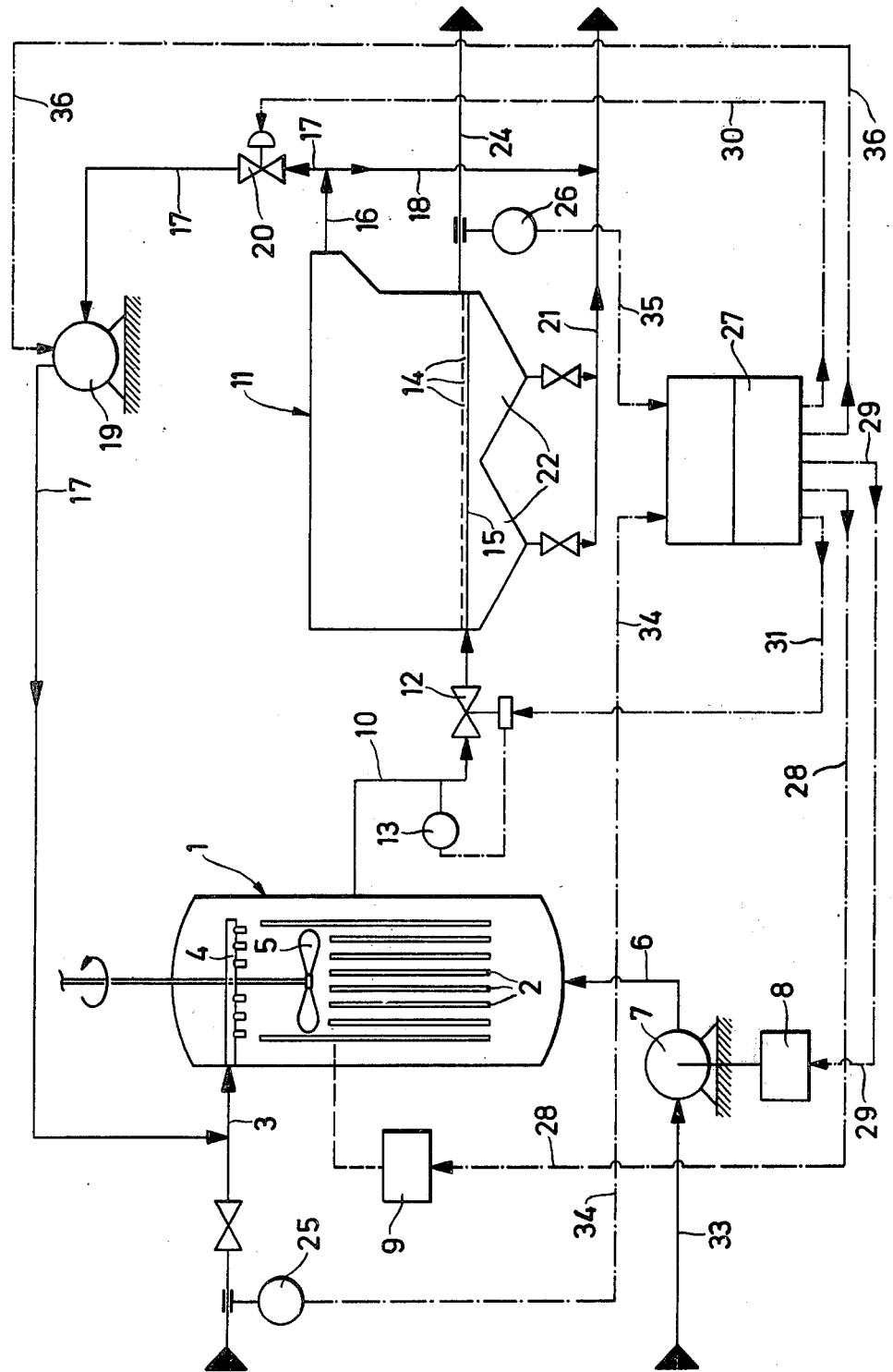

APPARATUS AND PROCESS FOR TREATING CONTAMINATED WATER

This invention relates to an apparatus and process for treating contaminated water and, particularly, contaminated water containing electrically-charged suspended particles.

It is known, for example from P. Treille "Utilisation de l'electricite en epuration d'eau" in R.G.E." (Revue Generale d'Electricite), 84, No. 4, April 1975, pages 315–320), to treat sewage, or the like, contaminated with impurities in the form of electrically charged suspended particles by electro-coagulation followed by subsequent flotation in order to decontaminate the sewage. In such processes, the contaminated water is acted upon by an electric field in an electro-coagulator with two results. First, the impurities which are present as electrically charged suspended particles are electrically discharged and coagulate. Secondly, the water is dissociated into hydrogen and oxygen. The coagulated particles are then separated from the liquid phase in a flotation tank while some of the gas bubbles evolved in the breakdown of the water accummulate on the coagulated suspended particles to improve the buoyancy of these coagulated particles and, therefore, their separation in a flotation tank. Further, some of the evolved oxygen is consumed by oxidizing the impurities. There is also a direct oxidation at the anodes of the coagulator so that it is possible to reduce the quantity of oxygen which has to be added at a later stage for chemical processes. An advantage of this process relative to the known floculation processes for the separation of particles in suspension is that there is no need to add to the effluent chemicals which require subsequent removal. However, the power consumption of these processes is relatively large. Further, another disadvantage is that the process must be performed intermittently and cannot be performed continuously.

Accordingly, it is an object of the invention to reduce the power consumption required for a sewage treatment procedure using electro-coagulation and flotation steps.

It is another object of the invention to provide a electro-coagulation water treatment process which can be performed continuously.

It is another object of the invention to provide a relatively simple means of continuously treating water using electro-coagulation and flotation.

Briefly, the invention provides an apparatus and process for treating contaminated water having electrically-charged suspended particles therein in which use is made of a controlled voltage.

The apparatus comprises an electro-coagulator, a voltage controller for controlling the voltage of the electro-coagulator, an inlet line connected to the electro-coagulator for delivering a flow of contaminated water, a flotation stage connected to the coagulator to receive a flow of treated water and an outlet line connected to the flotation stage for removing a flow of clarified water. In addition, a turbidity meter is disposed in at least one of the inlet line and outlet line for measuring the turbidity of the water flowing therethrough and for emitting signals in response to the measured values of turbidity. A controller is also connected to the turbidity meter to receive the signals and to the voltage controller in order to control the voltage controller in response to the received signals. In this regard, the voltage of the electro-coagulator is increased in response to an increase in turbidity and is decreased in response to a decrease in turbidity below a predetermined level.

In addition, the apparatus also comprises an air compressor which is connected to the electro-coagulator for delivering compressed air to the coagulator in response to an increase in turbidity. In this regard, the controller is also connected to the air compressor in order to activate the air compressor in response to an increase in turbidity in the water flowing into the coagulator or the clarified water flowing out of the outlet line of the flotation stage.

Still further, the apparatus includes a sludge return line which is connected to and between the flotation stage and the electro-coagulator in order to recycle a flow of sludge from the flotation stage to the electro-coagulator. A variable pump is also disposed in the sludge return line for pumping a variable amount of sludge to the coagulator. The controller is also connected to this pump in order to increase the rate of pumping in response to an increase in turbidity and to decrease the rate of pumping in response to a decrease in turbidity.

A pressure regulating means is disposed between the coagulator and the flotation stage in the flow of treated water therebetween for maintaining an increased pressure in the coagulator during operation of the air compressor.

The process of the invention comprises the steps of passing contaminated water through an inlet line into an electrical field in an electro-coagulator to discharge the electrically-charged particles in the water while simultaneously dissociating at least some of the water, and coagulating the discharge particles and thereafter separating the coagulated particles from the water in a flotation stage while removing a flow of clarified water from the flotation stage through an outlet line. In addition, the process includes the step of measuring the turbidity of the water flowing through at least one of the inlet line and the outlet line and of controlling the current density in the coagulator in response to the measured turbidity.

Should the turbidity in the water increase to such an extent that the voltage in the coagulator is increased above a top limit value, compressed air is introduced into the coagulator while the rate of flow of the sludge returned to the coagulator is increased. Thereafter, should there be a subsequent decrease in the voltage below a bottom limit value, the introduction of compressed air ceases while the rate of flow of the return sludge is reduced.

Thus, the invention provides an apparatus and process in which the turbidity of the clarified water serves as a controlled variable to vary the current density of the coagulator, the density increasing for excessive turbidity and vice versa. Since the flotation effect depends, inter alia, upon the number of gas bubbles produced and the number of bubbles, in turn, depends upon current density, the number of particles which are subject to flotation also increases as the current density increases and vice versa.

The measured values of the second turbidity measurement at the inlet line serve as command variables for the control procedure described above. This provides at least some compensation for the inertia of the apparatus within limits in response to alterations of the inflowing quantity of the suspended particles to the coagulator.

The intensity of the current flow between the electrodes of an electro-coagulator depends mainly upon the voltage across the electrodes and the conductivity of the electrolyte. Consequently, unless conductivity can be artificially increased, for example, by the addition of ionogenic substances, the only way of increasing current is to increase the voltage applied to the electrodes. However, for safety reasons, any such increase in voltage must be extremely limited. Hence, it is impossible to exceed a particular current strength or current density for a given conductivity of electrolyte. If such a density cannot provide the required cleansing, this state of affairs is manifested by an excessive turbidity in the outflowing clarified water. However, the introduction of compressed air into the coagulator at this time increases the supply of gas bubbles which help to increase the buoyancy of the particles to be flotated. This is because the liquid phase contains a relatively large quantity of gas in dissolved form at high pressure and, when the liquid phase subsequently expands into the flotation stage, a large number of gas bubbles separate out additionally. As a result, flotation by expansion is superimposed upon the flotation for which the electrically produced gas bubbles are responsible.

As in the case of sludge contact flocculation, so also in the present case, the increased quantity of returned sludge serves to improve separation of the very fine suspended particles by inclusion and accumulation on the relatively large lumps of flakes already present.

These and other objects and advantages of the invention will become more apparent from the following detailed description and appended claims taken in conjunction with the accompanying drawing in which:

The drawing schematically illustrates an apparatus in accordance with the invention.

Referring to the drawing, the apparatus for treating contaminated water containing electrically-charged suspended particles includes an electro-coagulator 1 and a flotation stage or tank 11. As shown, the coagulator 1 is provided with a plurality of electrodes 2 in known fashion. In addition, an inlet line 3 is connected to the coagulator 1 for delivering a flow of contaminated water to the coagulator 1. This inlet line 3 extends to a distributor 4 so as to distribute the contaminated water within the coagulator 1.

The electrodes 2 of the coagulator may have anodes made of lead-dioxide-coated titanium sheet while the cathodes are made of titanium.

The coagulator 1 also has a mechanical agitator 5 therein which provides a mechanical stirring of the liquid phase in the coagulator 1. The agitator 5 is driven by a drive (not shown) at a constant speed of, for example 500 revolutions per minute (rpm).

An air compressor 7 is connected to the bottom end of the coagulator 1 via a compressed air line 6 for delivering compressed air to the coagulator 1. As shown, the air compressor 7 has an intake line 33 for receiving air and a drive 8 which serves to drive the compressor 7.

Electricity is supplied to the coagulator 1 from a suitable power supply (not shown) via a voltage controller 9 which controls the voltage of the coagulator 1. The voltage controller 9 enables the voltage, and therefore, for a given conductivity of the liquid phase, the strength of the current flowing between the electrodes 2 to be varied.

A line 10 is disposed between the coagulator 1 and the flotation stage 11 in order to deliver treated water to the flotation stage 11. The line 10 also serves to convey the coagulated suspended particles and the gas-bubble containing liquid phase to the flotation stage 11. In addition, a pressure regulating means 12, for example, a solenoid valve, is disposed in the line 10 for purposes as described below. Also, a pressure sensor 13 is disposed in the line 10 and is connected to a controller for the valve 12.

The flotation stage serves to separate the coagulated impurities from the received water in known fashion. In this regard, the line 10 terminates in the flotation stage 11 in a distributing system for the liquid phase. This system includes various pipes, tubes, or the like 15 formed with orifices 14. The flotation stage 11 is of conventional structure and has an outlet 16 at the top for flotated sludge. This outlet 16 branches into a return line 17 and a removal line 18. The return line 17 is connected to the coagulator 1 in order to recycle a flow of sludge from the flotation stage 11 to the inlet line 3 to the coagulator. In addition, a variable pump is disposed in the sludge return line 17 for pumping a variable amount of sludge to the coagulator 1. A controllable stop valve 20 is also provided in the return line 17 upstream of the pump 19 in order to isolate the return sludge dispensing system from the complete system so that pump inspection and cleaning can be carried out safely.

The outlet line 18 serves to expel surplus sludge from the apparatus for further processing or upgrading. This line 18 extends to a second outlet line 21 which serves to remove precipitated sludge which accumulates in a funnel-shaped base 22 of the flotation stage 11.

An outlet line 24 is also connected to the flotation stage 11 for removing a flow of clarified water.

Turbidity meters 25, 26 are provided in the inlet line 3 and the outlet line 24 for measuring the turbidity of the water flowing through these lines and for emitting signals in response thereto. In addition, a controller 27 is connected to each of the turbidity meters 25, 26 via suitable signal lines 34, 35, respectively. The controller 27 is also connected via suitable lines 28–31 to the controller 9 for controlling the voltage of the electrodes 2, to the compressor drive 8, to the valve 20 in the sludge return line 17 and to the controller for the valve 12 in the line 10. The controller 27 is also connected via a signal line 36 to the variable pump 19.

The controller 27 controls the voltage controller 9 so as to cause an increase in the voltage across the electrodes 2 of the coagulator 1 in response to an increase in turbidity as measured by one or the other or both of the meters 25, 26 as well as a decrease in voltage in response to a decrease in turbidity below a predetermined level. In addition, should the voltage exceed a predetermined value, for example 12 volts, the controller 27 also effects activation of the air compressor 7, the valve 12, and the variable pump 19. In this regard, should the voltage increase over the predetermined top limit value, the air compressor 7 is activated to introduce compressed air into the coagulator 1. At the same time, the valve 12 is adjusted to maintain the increased pressure in the coagulator 1 during operation of the air compressor 7. Also, the variable pump 19 is adjusted to cause an increase in the rate of sludge return via the return line 17 to the coagulator 1. As the turbidity decreases, the controller 27 is programmed via the signal lines 34, 35 to shut off the air compressor 7 and thus cease the introduction of compressed air into the coagulator 1. In this regard, the compressed air is shut off when the voltage in the coagulator falls below a certain bottom limit value, which may be different from the top limit value noted above. At the same time, the valve 12 is opened to a greater degree and the variable pump 19 is reduced in speed to lower the rate of sludge return via the line 17.

The following example is given to further explain the operation of the apparatus.

An effluent from a board factory which is supplied via the line 3 has a suspended solids content of impurities of approximately 150 to 200 milligrams per liter (mg/l). Upon entry into the coagulator 1 in normal operation, i.e., without any supply of compressed air to the coagulator 1. A large proportion of the impurities or polutants is in the form of colloidal particles of less than 15 μm diameter and these particles must first be combined to form a separable, i.e., in the present case, floatable, larger particles by the coagulator 1 by means of technical processes and at a reasonable outlay in cost. At a maximum permissible voltage of 12 volts, the current densities in the coagulator 1 are from 1.1 to 2.5 A/dm$^2$ depending upon the conductivity of the effluent. Also, the agitator 5 runs at a constant speed of 500 rpm. Based upon these parameters, the apparatus produces approximately 4 5 liters of hydrogen per hour by the dissociation of water, the hydrogen being composed as gas bubbles which increase the flotation effect.

The average dwell time of the affluent in the coagulator 1 is approximately 30 minutes and depends upon how the coagulation process is performed. The dwell time in the flotation stage 11 depends on how long the separation takes and is about 20 minutes. The optimum values for both dwell times was found empirically.

During normal operation, approximately 5% of the sludge is returned through the sludge return line 17. The dry content of the sludge averages about 60 grams per liter (g/l).

Using the dwell times and characteristics given, a residual suspended solids content of from 15 to 20 milligrams per liter (mg/l) in the exiting clarified water can be achieved in the experimental apparatus. Thus, in normal operation, the process may remove approximately 90% of the solids polutants.

In this process, the oxidizing effect caused by the oxygen evolved in the dissociation of the water reduces the chemical oxygen requirement in subsequent purification stages by approximately 5 to 15%.

As stated above, the current flow through the electrodes 2 in the coagulator 1 is controlled in dependence upon the measured turbidity values in the clarified water outlet line 24. The measured values of turbidity measured in the meter 25 in the inlet line 3 are operative in the sense of an imposed interference as a command variable in order to make the control respond rapidly to changes in the suspended solids content of the entering effluent. As the suspended solids content increases, turbidity increases. The current flow through the electrodes 2 is therefore increased even though the turbidity meter 26 in the outlet line 24 has not started to call for an increase.

The controller 27 acts on the electrode voltage via the controller 9 so that at a given conductivity, changes occur in the current intensities which determine coagulation and the dissociation of water. When the maximum permissible voltage, 12 volts in the present case, is reached and the required cleansing effect has not been achieved, or when the command of variable indicates a considerable abrupt increase in suspended solids content, for example to an amount considerably above 200 milligrams per liter (mg/l) in the untreated affluent, a changeover occurs from normal operation to high load operation. In this regard, at high load operation, the air compressor 7 increases the pressure in the coagulator 1 to approximately 3 atmospheres while delivering a supply of compressed air thereto. In addition, the quantity of returned sludge is increased from 5% to approximately 10% by increasing the speed of the variable pump 19. At the same time that the compressor drive 8 is started, the valve 12 and the pressure sensor 13 are placed at standby by the controller 27. At the same time, the variable pump 19 delivery rate is increased.

The pressure of approximately 2 to 3 atmospheres absolute which the valve 12 maintains in the coagulator 1 is decreased on high load operations by expansion from the pipes 15 through the orifices 14 in the flotation stage 11. The high dissolved air content of the pressurized liquid phase is evolved in the form of additional gas bubbles and starts to act to provide expansion flotation.

When the measured turbidity values of the meters 25 and/or 26 drop below the minimum value in high load operation, such value being set in the controller 27, there is a changeover to normal operation. At this time the compressor stops, the standby stage of the valve 12 is cancelled and the valve 12 opens fully while the return sludge quantity decreases. Also, the controller 9 acts to reduce the electrode voltage below its peak value so that normal control, as described above, can be restored.

What is claimed is:

1. A process for treating contaminated water having electrically-charged suspended particles therein, said process comprising the steps of passing the contaminated water through an inlet line into an electrical field in an electro-coagulator to discharge the electrically-charged particles while simultaneously dissociating at least some of the water;

coagulating the discharged particles;

thereafter separating the coagulated particles from the water in a flotation stage and removing a flow of clarified water from the flotation stage through an outlet line;

measuring the turbidity of the water flowing through at least one of the inlet line and the outlet line; and controlling the current density in the coagulator in response to the measured turbidity whereby the voltage of said electro-coagulator is increased in response to an increase in turbidity and decreased in response to a decrease in turbidity below a predetermined level.

2. A process as set forth in claim 1 which further comprises the step of returning a flow of sludge from the flotation stage to the electro-coagulator.

3. A process as set forth in claim 2 which further comprises the steps of introducing compressed air into the electrocoagulator in response to an increase in voltage in the coagulator above a top limit value while increaseing the rate of flow of the sludge returned to the coagulator from the flotation stage; and ceasing the introduction of compressed air into the coagulator in response to a subsequent decrease in voltage in the coagulator below a bottom limit value while reducing the rate of flow of the sludge returned to the coagulator from the flotation stage.

* * * * *

UNITED STATES PATENT AND TRADEMARK OFFICE
CERTIFICATE OF CORRECTION

PATENT NO. : 4,123,341
DATED : October 31, 1978
INVENTOR(S) : Jurgen Gnieser et al It is certified that error appears in the above-identified patent and that said Letters Patent are hereby corrected as shown below:

Column 5, line 23, change "45" to --4 to 5--

Signed and Sealed this

Fifth Day of June 1979

[SEAL]

Attest:

RUTH C. MASON
Attesting Officer

DONALD W. BANNER
Commissioner of Patents and Trademarks